United States Patent [19]

Ichikawa et al.

[11] 4,426,290

[45] Jan. 17, 1984

[54] APPARATUS FOR SEPARATING BLOOD

[75] Inventors: Toshiji Ichikawa, Chofu; Teruko Watanabe, Tokyo; Yoshimitsu Asada, Honmachi, all of Japan

[73] Assignee: Terumo Corporation, Tokyo, Japan

[21] Appl. No.: 473,975

[22] PCT Filed: Sep. 11, 1980

[86] PCT No.: PCT/JP80/00206

§ 371 Date:

§ 102(e) Date:

Related U.S. Application Data

[63] Continuation of Ser. No. 259,027, Apr. 30, 1981, abandoned, which is a continuation-in-part of Ser. No. 184,084, Sep. 4, 1980, Pat. No. 4,310,430.

[30] Foreign Application Priority Data

May 8, 1980 [JP] Japan ............................ 55-61013
May 26, 1980 [JP] Japan ............................ 55-69913
Mar. 12, 1981 [JP] Japan ............................ 56-34636

[51] Int. Cl.$^3$ .................... B01D 21/26; C09K 3/00
[52] U.S. Cl. ................... 210/516; 210/782; 210/789; 210/927; 252/60; 422/101; 436/177; 436/178
[58] Field of Search ............ 436/177, 178; 422/56, 58, 59, 61, 101, 102; 210/782, 787, 789, 927, 514, 515, 516, 517, 518; 252/60

[56] References Cited

U.S. PATENT DOCUMENTS

| | | | |
|---|---|---|---|
| 3,780,935 | 12/1973 | Lukas | 210/927 |
| 3,920,549 | 11/1975 | Gigliello | 210/789 |
| 3,981,804 | 9/1976 | Gigliello | 210/789 |
| 3,997,442 | 12/1976 | Gigliello | 210/927 |
| 4,021,340 | 5/1977 | Zine | 252/60 |
| 4,056,468 | 11/1977 | Breiter | 210/927 |
| 4,071,316 | 1/1978 | Wright | 210/927 |
| 4,101,422 | 7/1978 | Lamont | 210/927 |
| 4,147,628 | 4/1979 | Bennett | 210/789 |
| 4,172,803 | 10/1979 | Ichikawa | 210/927 |
| 4,180,465 | 12/1979 | Murty | 210/927 |
| 4,189,382 | 2/1980 | Zine | 210/927 |
| 4,235,725 | 11/1980 | Semersky | 210/927 |
| 4,310,430 | 1/1982 | Ichikawa | 252/60 |

Primary Examiner—Ernest G. Therkorn
Attorney, Agent, or Firm—Frishauf, Holtz, Goodman & Woodward

[57] ABSTRACT

An apparatus for separating blood is provided with a closed end and a thixotropic gel-like sealant with a specific gravity intermediate between the gravities of serum and clot phases. A cavity is formed on the upper surface of said sealant. The sealant consists essentially of an α-olefin-dimaleate copolymer having a viscosity from 10,000 to 120,000 c.p. (25° C.), to which a viscosity-specific gravity adjusting agent is added to adjust the specific gravity to 1.035–1.055. The cavity is formed in such a size that diameter of the upper surface is from 0.15 to 0.7 times the inner diameter of the apparatus and its depth is from 0.13 to 0.65 times the thickness of said sealant.

25 Claims, 9 Drawing Figures

APPARATUS FOR SEPARATING BLOOD

CROSS REFERENCE TO RELATED APPLICATION

This application is a continuation of application Ser. No. 259,027, filed Apr. 30, 1981, now abandoned, which in turn is a continuation-in-part of U.S. Appln. Ser. No. 184,084, filed Sept. 4, 1980, now U.S. Pat. No. 4,310,430, issued Jan. 12, 1982.

BACKGROUND OF THE INVENTION

Field of the Invention

This invention relates to an apparatus for separating blood into serum and clot phases by centrifugal separation.

Description of the Prior Art

Heretofore has been known a device for separating blood containing a thixotropic gel-like sealant, for example, a mixture consisting of silicone oil, silica and a gelling agent, at the bottom of a blood-collecting tube (U.S. Pat. No. 3,780,935). A volume of blood is collected in the blood-separation tube and, after being allowed to stand for an appropriate period of time, is subjected to centrifugal separation. The centrifugal force induces flow of the sealant and, due to its specific gravity being intermediate between serum and the clot portion, the sealant is gradually moved upward from the bottom of the tube eventually to a position intermediate the serum and clot layers, thereby enabling separation of the serum and clot layers. Such method, however, requires a considerably large centrifugal force, for example, 1500 G, when serum is to be separated from a small amount of blood. The large centrifugal force will cause injuries to blood cells to cause hemolysis, and it is occasionally problematic that correct biochemical test data cannot be obtained. The problem is especially influential when the gel-like material is made of a substance in which hardening of the gel proceeds with elapse of time due, for example, to formation of hydrogen bonds and which is liable to deterioration in flow behaviors.

In order to overcome the above-mentioned problem, a blood-separation tube has been devised in which the sealant as described above has a slant surface so that the sealant is readily flowable upon centrifugal separation (U.S. Pat. No. 3,997,442).

In such prior-art blood-separation tube, however, it is necessary in order to produce satisfactory flowability to have the upper surface of the sealant being slant at a considerably large angle. The upper surface slanted at a larger angle will suffer from a deficiency of being broken during transportation or handling of the product. It is also disadvantageous that the manufacturing line for forming such a slant surface is complex and costly because it requires an operation, for example, centrifugal operation which should be carried out not on a continuous basis but on a batch basis.

The sealant consisting of silicone oil, silica and a gelling agent is also associated with problems. It is produced by mechanically mixing the components which are poorly compatible one another and in which the gelling agent promotes formation of a hydrogen bond between silica particles (a specific gravity-adjusting agent) to produce thixotropic gel. It is therefore a matter of concern that the hydrogen bond becomes stronger as time elapses eventually to cohesion which results not only in phase segregation but also in poor flowability during the centrifugal operation. Whereas it has been proposed that a surfactant is incorporated to prevent the phase segregation, the ionic surfactant, if incorporated in a large portion, will produce another problem of hemolysis.

Moreover, other problems associated with the prior art compositions are that, when the above-cited composition is subjected to γ-ray sterilization while contained in an appropriate amount in a blood-collecting tube, a marked change in character is induced, for example, by cross-linking to deteriorate performance as the sealant, that low-molecular substances in the gel-like material evaporate to make the inner surfaces of the tube water-repellent thereby bringing about delay in blood coagulation and adhering the clots to the inner surface, and that the raw materials are relatively expensive.

In addition to the above, a sealant consisting of a gel-like material based upon a polyester is known. As with the above-described prior-art gel-like materials, however, the sealant is also associated with problems such as delay in blood coagulation and clot adherence due to water-repellency on the inner surface of the tube made by the sealant as well as unpleasant odor produced.

It is therefore an object of this invention to provide a novel and improved apparatus for separating blood free from such disadvantages as set forth above.

SUMMARY OF THE INVENTION

First, the present invention provides an apparatus for separating blood wherein blood separation is operable using a thixotropic gel-like sealant under the influence of a centrifugal force smaller than the forces used in the prior art while eliminating the problem of hemolysis.

There is provided in the present invention an apparatus for separating blood provided with a tube with a closed end and a thioxtropic gel-like sealant having a specific gravity intermediate between the gravities of serum and clot phases a said sealant being contained at the bottom of said tube with a cavity formed on its upper surface.

Furthermore, the invention provides an apparatus for separating blood as defined above wherein a cavity is formed in such a size that the diameter of the upper surface is from 0.15 to 0.7 times the inner diameter of the bue and the depth of the cavity is from 0.13 to 0.65 times the thickness of the sealant (at the thickest portion at the center).

Second, the present invention provides an apparatus for separating blood containing a sealant which is stable on aging by using an oil of large dispersing capacity, can be subjected to γ-ray sterilization, exerts almost no water-repellency, is free from unpleasant odor, is manufactured at a lower cost, produces no hemolysis and, when contained in the blood-collecting tube in advance, causes no delay in coagulation and no adhesion of the clots to the inner wall.

This invention, thirdly, provides an apparatus for separating blood which contains in a space within the blood-separation tube above the sealant contained at the bottom of said tube a clot-promoting agent held on the carrier to promote clotting.

DETAILED DESCRIPTION OF THE PREFERRED EMBODIMENTS

Figure 1:
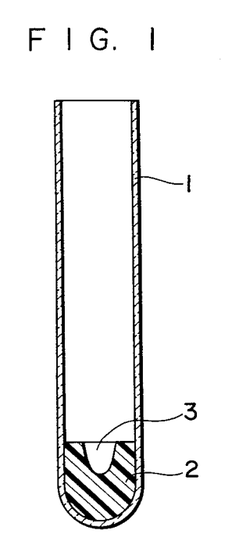
FIG. 1 is a sectional view illustrating an example of the apparatus for separating blood according to the present invention.

FIG. 1 shown an example of the apparatus for separating blood according to the present invention wherein at the bottom of a separation tube 1 (a 10-ml. tube) is contained a thixotropic gel-like material 2 (for example, silicone oil/silica, α-olefin-dimaleate copolymer/filler, liquid polybutadiene/filler or epoxydized polybutadiene/filler) in a depth of about 15 mm. At the center on the upper surface is formed a generally cylindrical cavity 3 (diameter of the opening 4 mm. and depth 3 mm.). Since the generally cylindrical cavity 3 is defined in the thixotropic material, there is no possibility for the cavity to be substantailly collapsed during ordinary transportation and handling.

Figure 2:
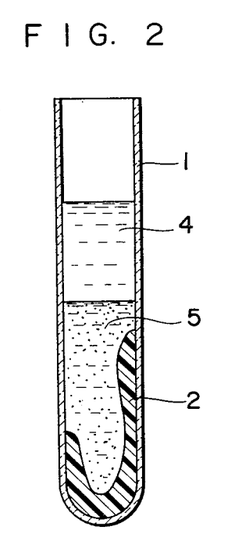
FIGS. 2 to 4 are sectional views stepwise indicating flows of the gel-like sealant when the apparatus for separating blood is subjected to centrifugal separation operation.

The separation tube is similar in shape to the prior-art tubes except that there is a cavity 3 formed as described above. The tube is prepared with an open end tightly closured and the inside evacuated. An end of a venopuncture needle (not shown) is pierced through the closure for collecting blood. After the blood collection, the tube is left to form a clot and is subjected to a centrifugal separation operation, and the gel-like material 2 is fluidized by the centrifugal force. As shown in FIG. 2, the cavity 3 is further expanded, and the material is transformed in such a manner that a portion of the material is moved upward along the wall of the tube. Subsequently, as shown in FIG. 3, the material is forced to flow toward the interface between the serum layer 4 and the clot layer 5, eventually forming a layer of the sealant 2 uniform in thickness between the serum layer 4 and the clot layer 5 as shown in FIG. 4.

Figure 3:
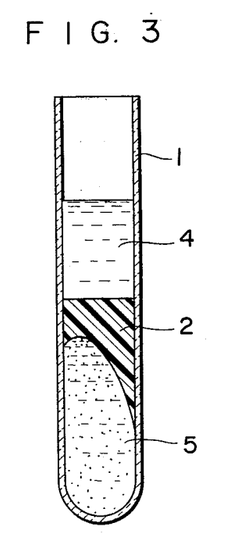
Figure 4:
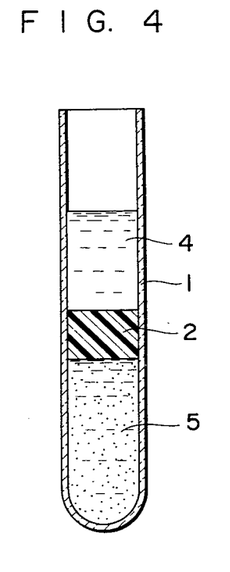

Even with the prior-art apparatus for separating blood which contain a gel-like sealant without a cavity 3 within the separation tube, the flat upper surface of the gel-like sealant becomes curved, strain is produced and exaggerated and flow of the sealant becomes greater in such a manner as shown in FIGS. 1–3. A separation layer is eventually formed as shown in FIG. 4. However, in the prior-art processes is required a large stress for forming the strain at the first stage. According to the present invention, on the other hand, the centrifugal separation is carried out for the gel-like sealant with strain (that is, a cavity) formed in advance so that the gel-like sealant is easily fluidized by a stress smaller than the one requied for the prior-art processes.

Figure 5:
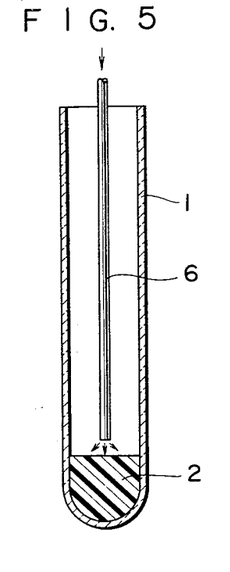
FIG. 5 is a sectional view for describing the method of preparinhg the apparatus for separating blood according to the invention.

Any means may be selected for forming a cavity on the upper surface of the sealant contained at the bottom of the separation tube depending upon physical properties of the sealant and other conditions. As shown in FIG. 5, for example, the cavity can easily be formed by jetting a fluid such as air or liquid toward the surface of the gel-like sealant.

Figure 6:
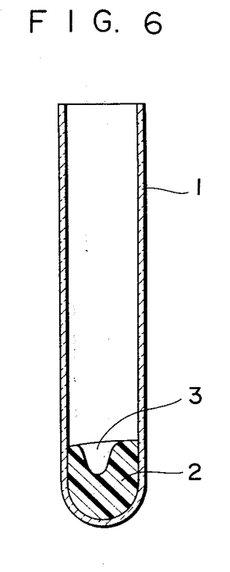
FIGS. 6 and 7 are sectional views of the apparatus relating to other examples of the present invention.
Figure 7:
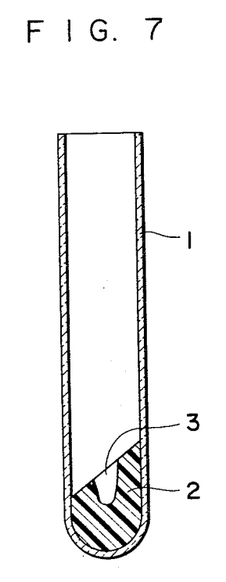

The cavity formed upon the surface of the gel-like sealant may be at any position and in any shape. For example, in addition to an example shown in FIG. 1, the cavity 3 may be formed at the center or a position closer to one of the walls of the tube as shown in FIG. 6. Alternatively, as shown in FIG. 7, the gel-like material 2 may be filled asymmetrically with a slant upper surface on which the cavity 3 may be formed. In addition to the generally cylindrical cavity as described above, the cavity may optionally be in a variety of forms such as a cone or a prism. It is essential that stress in centrifugal separation is concentrated at the cavity to produce strain in the gel-like material and the shear force is provided.

The cavity may also be of various sizes. Even if the cavity is in a smaller size, it induces promotion of the fluidization of the gel-like material by the action as described above. In general, however, the diameter of the opening of the cavity is preferably from 0.15 to 0.7 times, more preferably from 0.3 to 0.5 times the inner diameter of the tube, and the depth of the cavity is preferably from 0.13 to 0.65 times, more preferably from 0.2 to 0.55 times the thickness of the gell-like material. When the diameter of the opening of the cavity is below 0.15 times the inner diameter of the tube, and if the depth is below 0.13 times the thickness of the gell-like material, there will be produced a nearly flat gel. If the latter is above 0.65 times, the cavity will be difficult to form and difficult to maintain its shape. Also, when the diameter of the opening of the cavity is above 0.7 times the inner diameter of the tube, and if the depth is below 0.13 times the thickness of the gell-like material, there will be produced a nearly flat gel. If the latter is above 0.65 tmes, there will be no site upon which the stress is applied.

A preferred sealant employed in the present invention is that which consists as the principal component of an α-olefin-dimaleate copolymer having a viscosity from 10,000 to 120,000 c.p. at 25° C. to which a viscosity-specific gravity adjusting agent is added.

As typical examples of the α-olefin-dimaleate copolymer used as the sealant component in the present invention are mentioned copolymers having a viscosity from 10,000 to 120,000 c.p. at 25° C. and represented by the general formula wherein $R_1$ may be the same or different in one molecule and is hydrogen atom or an alkyl group containing from 1 to 20 carbon atoms, $R_2$ and $R_3$ are each a straight or branched alkyl group containing from 1 to 15 carbon atoms or a branched alkyl group containing from 16 to 20 carbon atoms, provided that when $R_1$ is a hydrogen atom, $R_2$ and $R_3$ are each a straight or branched alkyl group containing from 12 to 15 carbon atoms or a branched alkyl group containing from 16 to 20 carbon atoms, and when $R_1$ is an alkyl group having from 1 to 20 carbon atoms, the total numbers of carbon atoms in $R_1$ and $R_2$ groups and $R_1$ and $R_3$ groups are from 5 to 25, respectively, and n is an integer in such a range as allowing viscosity of said copolymer to be from 10,000 to 120,000 c.p. at 25° C., for example, from 5 to 30.

In the above formula, $R_1$ is preferably an alkyl group containing from 2 to 20 carbon atoms, $R_2$ and $R_3$ are each preferably selected from the group consisting of methyl, ethyl, butyl and 2-ethylhexyl groups and n is preferably an integer in such a range as allowing viscosity of said copolymer to be from 10,000 to 120,000 c.p., preferably from 40,000 to 80,000 c.p. (25° C.), for example, from 8 to 12.

α-Olefin-dimaleate copolymers represented by the above formula wherein $R_1$, $R_2$, $R_3$ and n are other than those defined above do not give the desired viscosity.

Preferred numbers of carbon atoms of α-olefin component are in the range between 4 and 22.

α-Olefine-dimaleate copolymers of an α-olefin component having from 30 to 60 carbon atoms with a dimaleate wherein $R_2$ and $R_3$ allow crystallization of said copolymers, are waxy and, accordingly, cannot be used as the principal component of the present sealant. They, however, can be used as an additive to prevent reduction of thixotropy caused by phase segregation in the sealant.

The above α-olefin-dimaleate copolymer is light yellow in color, transparent, odorless, non-interactive with blood so that there is no influences to blood, stable for a long period of time and releases little water-repellent substances so that, when contained in a blood-collecting tube, inner surfaces of the tube can be kept clean. When subjected to radiation sterilization for example, employing γ-ray, substantially no physical or chemical changes take place.

Specific gravity of the α-olefin-dimaleate copolymer used as the sealant in the invention is in the range between 1.00 and 1.038 and preferably between 1.027 and 1.035.

Preferred specific gravity-viscosity adjusting agents used in the present invention are aliphatic amine derivatives of smectite clay. Illustration are primary, secondary, tertiary and quaternary aliphatic amine derivatives of smectite clay. The amine derivatives are known substances. Particularly preferred are quaternary aliphatic amine derivatives of smectite clay. More specifically, $C_8$–$C_{24}$ aliphatic amine derivatives of smectite clay such as Bentone 34, Bentone 38, Bentone 27 and Bentone 128 (quaternary ammonium salt derivatives of smectite clay manufactured by NL Industry Co.) may be employed.

Other examples of the viscosity-specific gravity adjusting agent used in this invention are inorganic fine powders. For example, fumed silica or precipitated silica is selected as desired. The viscosity-specific gravity adjusting agent is employed in such an amount as producing satisfactory gelation and a predetermined specific gravity depending upon specific gravity and viscosity of the principal component.

A gelling agent is used in the present invention in order to achieve gelation of the sealant and additionally to keep the gelled state stable. Depending upon the physical properties of the principal component and the viscosity-specific gravity adjusting agent of the invention, the gelling agent is employed for producing gelation. For exzample, dimethylpolysiloxane polyoxyalkylene copolymers such as SH-3771, SH-190 and SH-192, trade names, manufactured by Toray Silicone Co., Ltd., carbitols such as ethylene diglycol and the like may be used.

The amount of the gelling agent employed is dependent upon combination of the principal component and the viscosity-specific gravity adjusting agent of the invention and should be such that the gelation is achieved and that no gelling agent will be segregated from the other components.

According to the present invention, in addition to the α-olefin-dimaleate copolymer, the viscosity-specific gravity adjusting agent and the gelling agent, a nonionic surfactant such as, for example, polyoxyethylene hydrogenated caster oil monolaurate or polyoxyethylene hydrogenated caster oil triisostearate may be added, as required.

Addition of the surfactant in a small amount, for exaple, 0.47–2.7% by weight, will prevent phase segregation which is likely when allowed to stand for a long period of time. There is no possibility for hemolysis or other adverse reactions to occur because of its non-ionic nature. It is especially useful when silica alone is used as the viscosity-specific gravity adjusting agent.

Examples of the composition of the sealant used in the present invention are given in Tables 1 and 2 below. In the tables, the α-olefin-dimaleate copolymer (A) is an n-α-olefin-dimethyl maleate copolymer consisting of a combination of α-olefin components of 12 and 14 carbon atoms, which has an average molecular weight of 3,000–4,000, a specific gravity of 1.027–1.035 (25° C.) and a viscosity of 40,000–120,000 c.p. (25° C). The copolymer (B) is an n-α-olefin-dimethyl maleate copolymer consisting of a combination of α-olefin components of 6 and 8 carbon atoms, which has an average molecular weight of 2,000–3,000, a specific gravity of 1.035 (28° C.) and a viscosity of 10,000–120,000 c.p. (25° C.). The copolymer (C) is an n-α-olefin-dimethyl maleate copolymer wax consisting of α-olefin components of 30–60 carbon atoms. The copolymer (D) is an n-α-olefin-diethyl maleate copolymer consisting of a combination of α-olefin components of 16 and 18 carbon atoms, which has an average molecular weight of 3,600–4,000, a specific gravity of ca. 0.995 (28° C.) and a viscosity of ca. 10,000 c.p. (28° C.).

The copolymer (E) in Table 2 is an n-α-olefin-dimethyl maleate copolymer consisting of α-olefin components of 12 and 14 carbon atoms, trade name PAR-124 manufactured by Mitsubishi Chemical Industries Co., Ltd. which has an average molecular weight of 2,000–3,000, a specific gravity of 1.00–1.03 (28° C.) and a viscosity of 10,000–20,000 c.p. (28° C.).

In addition to the above, n-α-olefin-dibutyl maleate copolymer and n-α-olefin-di-2-ethylhexyl maleate copolymer and the like may be employed as the α-olefin-dimaleate copolymer.

TABLE 1.

| | Examples of the composition (parts by weight) Composition No. | | | | | | | |
|---|---|---|---|---|---|---|---|---|
| | 1 | 2 | 3 | 4 | 5 | 6 | 7 | 8 |
| α-Olefine-dimaleate | | | | | | | | |
| copolymer (A) | 100 | 100 | 100 | 100 | 50 | — | — | — |
| copolymer (B) | — | — | — | — | 50 | 100 | — | — |

TABLE 1.-continued

| | Examples of the composition (parts by weight) Composition No. | | | | | | | |
|---|---|---|---|---|---|---|---|---|
| | 1 | 2 | 3 | 4 | 5 | 6 | 7 | 8 |
| copolymer (C) | — | — | 10 | 30 | — | — | — | — |
| copolymer (D) | — | — | — | — | — | — | 100 | 100 |
| Aerosil R-972* | — | — | 2.0 | 2.0 | 1.0 | — | 1.5 | — |
| Aerosil 200** | 1.0 | 1.0 | — | — | — | — | — | — |
| Bentone 38*** | — | 1.0 | 1.0 | — | — | 2.0 | 10.0 | — |
| Bentone 34*** | — | — | — | — | 1.0 | — | — | 12.0 |
| Bentone 27*** | 3.0 | — | — | — | — | — | — | — |
| Bentone 128*** | — | — | 2.0 | — | — | — | — | — |
| Specific gravity | 1.047 | 1.039 | 1.052 | 1.040 | 1.042 | 1.043 | 1.041 | 1.041 |
| Viscosity ($\times 10^4$ c.p./25° C.) | 53 | 62 | 58 | 43 | 57 | 75 | 64 | 69 |
| Hemolysis | None | None | None | None | None | None | None | None |
| Adherence of the clots | " | " | " | " | " | " | " | " |

*Hydrophobic silica fine powders, average particle size ca. 16 mμ, apparent specific gravity ca. 60 g./l., manufactured by Nippon Aerosil Co., Ltd.
**Hydrophilic silica fine powders, average particle size ca. 12 mμ, apparent specific gravity ca. 60 g./l., manufactured by Nippon Aerosil Co., Ltd.
***Quaternary ammonium salt derivative of smectite clay, manufactured by NL Industry Co., U.S.A.

TABLE 2

| | Examples of the composition (parts by weight) Composition No. | | | | | |
|---|---|---|---|---|---|---|
| | 9 | 10 | 11 | 12 | 13 | 14 |
| α-Olefine-dimaleate | | | | | | |
| copolymer (E) | 100 | 100 | 100 | 100 | 100 | — |
| copolymer (B) | — | — | — | — | — | 100 |
| copolymer (C) | — | — | 50 | 50 | — | — |
| Aerosil R-972* | 6.0 | — | 7.0 | 5.0 | 7.0 | — |
| Aerosil 200** | — | 6.0 | — | 1.0 | — | 2.0 |
| Surfactant*** | 0.5 | 1.0 | 1.0 | — | 1.0 | 3.0 |
| Gelling agent**** | 0.18 | 0.04 | — | 0.2 | 0.5 | 0.6 |
| Specific gravity | 1.042 | 1.042 | 1.045 | 1.040 | 1.045 | 1.042 |
| Viscosity ($\times 10^4$ c.p./25° C.) | 54 | 80 | 73 | 68 | 52 | 51 |
| Hemolysis | None | None | None | None | None | None |
| Adherence of the clot | " | " | " | " | " | " |

*See Table 1.
**See Table 1.
***Polyoxyethylene hydrogenated caster oil monolaurate, manufactured by Nihon Emulsion Co., Ltd.
****SH-3771, dimethylpolysiloxane-polyoxyalkylene copolymer, manufactured by Toray Silicone Co., Ltd., specific gravity 1.060–1.080 (°C.), viscosity 260–280 c.p.

Next, the method for preparing the sealant used in the present invention will be described below.

First, the preparative method of α-olefin-dimaleate copolymers is described. Ethylene is polymerized to a low degree of polymerization to give n-α-olefins, which are fractionated into those containing, for exaple, 4, 6, 8 and 10, 12 and 14, 16 and 18 and from 30 to 60 carbon atoms, respectively. Depending upon viscosity, nature of the specific gravity-adjusting agent and specific gravity, they may be employed alone or in combination. When they are used for separating serum, those containing 12 and 14 or 6 and 8 carbon atoms are preferred in view of their viscosity and specific gravity. n-α-olefins having an odd number carbon atoms may be obtained by cracking n-α-olefins obtained above. Then, a copolymerization with a dimaleate is effected to give the desired product.

Subsequently, to the α-olefin-dimaleate copolymer basic material which has a viscosity of 10,000–120,000, preferably 40,000–80,000 c.p. (25° C.) are added a viscosity-specific gravity adjusting agent such as an aliphatic amine derivative of smectite clay or silica fine powders and, optionally as required, a gelling agent, a non-ionic surfactant and a waxy α-olefin-dimaleate copolymer, for example, the one in which the n-α-olefin contains from 30 to 60 carbon atoms. The mixture is then kneaded using a roll mill, a grinding mill, a planetary mixture or the like, thereby providing an appropriate shear force to gelation.

The sealant thus prepared preferably has a viscosity from 250,000 to 800,000 c.p. (25° C.) and a specific gravity from 1.035 to 1.055. Any of the compositions illustrated in the tables above is of thixotropic nature, exerts fluidity with stress such as centrifugal force and, under normal conditions, forms homogeneous and stable gel.

As clearly seen from Tables 1 and 2 above, the sealant never makes the inner surfaces of the tube water-repellent when in advance contained in the tube with a result that there is caused neither adhesion of the clot nor delay in coagulation of the blood. This is because an α-olefin-dimaleate copolymer is used so that no low-molecular volatile substances are formed. Therefore, when the sealant according to the invention is used in the blood-collecting vessel, a stable seal can be produced between serum and clot by subjecting it to centrifugal separation using an ordinary centrifugal force (700–1,000 G) for about 10 minutes. It is consequently feasible that serum is easily isolated by decantation without fibrin and other containations. After the centrifugal separation, the sealant remains a stable gell between serum and clot and no intermixture between the serum and the clot after separation occurs during transportation, for example, from a hospital to a clinical laboratory.

Moreover, the present invention provides an apparatus for separating blood which contains, in a space within the blood-separation tube above the sealant contained at the bottom of said tube, a clot-promoting agent-holding carrier thereby promoting clotting.

The carrier used in the aforementioned separation tube may be a hydrophilic carrier with a specific gravity higher than that of blood cells which holds with a binder soluble in serum an appropriate amount of a powdery clot-promoting agent.

The carrier may be cloth, filter paper, nonwoven cloth, cotton ball and the like in any form. It is essential that it has a specific gravity higher than that of blood cells, it is not hemolysis-inducing, it does not interfere with biochemical tests, it is composed of a water-holding material, for example, hydrophilic one, or has a water-holding structure, for example, a porous structure with continuous pores, it is sufficiently rigid or elastic to be held between the walls of the tube and, at the same time, sufficiently soft to be migrated to the clot layer by stress during centrifugal separation and it is of a size sufficiently small to be submerged in the blood cell layer.

Any of those clot-promoting agents which are not substantially hemolysis-inducing and are dispersed in blood may be employed. For example, silica with a particle size from 0.4 to 20 microns, crystalline silica with a particle size of 5 microns or below and on average 1.1 microns such as one manufactured by Pensylvania Glass Sand Co. under the trade name MIN-U-SIL, diatomaceous earth, glass fine powders, Kaolin, bentonite and the like may be employed.

The clot-promoting agent held in the carrier is used in an amount from 0.3 to 10.0 mg. per 10 ml. of the collected blood. An excess amount of the agent will induce hemolysis, and a smaller amount of the agent will not be sufficient to effectively promote clotting.

A suitable amount of the clot-promoting agent added to the carrier can easily be controlled by the amount of a binder solution as discussed below to which an appropriate amount of the clot-promoting agent is added.

It is essential that the binder be soluble in serum. This is because the binder should be dissolved as soon as blood is collected to rapidly disperse the clot-promoting agent in the blood so that formation of clot is promoted. It is also desirable that the binder be suitably sticky, not volatile, serologically inactive and able to be subjected to sterilization operation, such as γ-ray irradiation, without changes in activity. Examples of the binder are water-soluble silicone, polyethylene glycol, polyvinylpyrrolidone, dextran and cellulose derivatives such as carboxymethylcellulose, hydroxypropylcellulose and methylcellulose. Cellulose derivatives and polyvinylpyrrolidone are most preferable because of their good solubility and hygroscopicity. Dextran is somewhat inferior due to its lower solubility. Polyethyleneglycol is not preferable if kept in open air for a long period of time after preparation because it is hygroscopic.

Production of a medium such as nonwoven cloth containing a predetermined amount of the clot-promoting agent can easily be carried out by a dipping process. Examples of the carriers to which a clot-promoting agent is applied by a dipping process and composition of the bath are shown in Table 3.

TABLE 3

| Carrier | Composition of the bath | |
|---|---|---|
| | Clot-promoting agent (% by weight) | Binder (% by weight) |
| 20603 FLO (Polyester manufactured by Unichika Co., Ltd.) | Min-U-Sil (8.0%) (Crystalline silica manufactured by Pensylvania Glass Sand Co.) | SH 3771 (0.2%) (Manufactured by Toray Silicone Co., Ltd.) |
| 5050 (Nylone manufactured by Asahi Chemical Industries Co., Ltd.) | Min-U-Sil (7.5%) (Crystalline silica manufactured by Pensylvania Glass Sand Co.) | SH 3771 (0.2%) (Manufactured by Toray Silicone Co., Ltd.) |
| ED 972 (Rayon 80/ Olefin 20, JAPAN VILENE COMPANY LTD.) | Flattery Sand (1.0%) (Manufactured by KYORITSU CERAMIC MATERIALS COMPANY LTD.) | SH-190 (0.05%) (Toray Silicone Co., Ltd.) |
| 1200 (Rayon 80/ Olefin 20) (Fuji Chemicloth Co., Ltd.) | Flattery Sand (3.0%) (Manufactured by KYORITSU CERAMIC MATERIALS COMPANY LTD.) | SH-190 (0.005%) (Toray Silicone Co., Ltd.) |
| 800 (Rayon 80/polyester 20) (Fuji Chemicloth Co., Ltd.) | Flattery Sand (5–10%) (Manufactured by KYORITSU CERAMIC MATERIALS COMPANY LTD.) | [Polyethylene glycol (5–10%)] |
| 312-41T (Toray Co., Ltd. polyester) | Flattery Sand (5–10%) (Manufactured by KYORITSU CERAMIC MATERIALS COMPANY LTD.) | [Polyethylene glycol (5–10%)] |
| 312-41T (Toray Co., Ltd. polyester) | Flattery Sand (5–10%) (Manufactured by KYORITSU CERAMIC MATERIALS COMPANY LTD.) | PVP (0.5–2%) |
| 312-41T (Toray Co., Ltd. polyester) | Flattery Sand (5–10%) (Manufactured by KYORITSU CERAMIC MATERIALS COMPANY LTD.) | HMPC (0.5–2%) |

An embodiment of the present invention wherein the apparatus for separating blood contains, in a space within the blood separation tube above the sealant contained at the bottom of said tube, a clot-promoting agent-holding carrier to promote clotting is given below.

Figure 8:
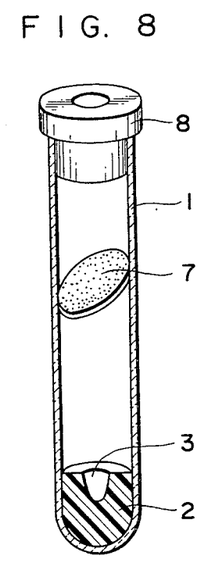
FIG. 8 is a partly sectional view illustrating an example of the apparatus for separating blood according to the invention which is provided with a clot-promoting medium and FIG. 9 is a sectional view of the apparatus for separating blood after a centrifugal operation on the apparatus for separating blood shown in FIG. 8.
Figure 9:
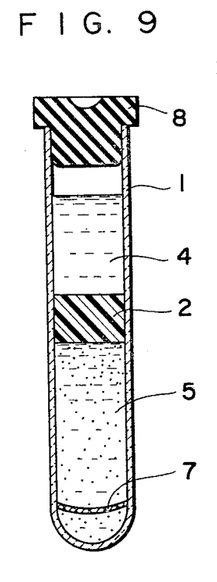

As shown in FIG. 8, each of the liquid sealants 2 of the compositions 1–12 about 17 ml. in volume was placed at the bottom of a 10-ml. blood-collecting tube 1. A cavity 3 was formed on the upper surface of the sealant, and a piece of polyester nonwoven cloth 7 holding 0.3–10.0 mg. of silica (for example, Cape Flattery Sand, trade name WG-200, manufactured by KYORITSU CERAMIC MATERIALS COMPANY LTD. was placed in a slanted position intermediate the bottom and the open end of the tube. The tube was then sealed with a butyl rubber closure 8 and evacuated. Subsequently, blood was siphoned into each blood-collecting tube by venipuncture, and the tube was allowed to stand for 7–8 minutes. Introduction of the blood forced the silica to disperse in the blood to promote, in cooperation with the nonwoven cloth 7, clotting of the blood sufficiently to complete in such short period of time. Each separation tube was then subjected to centrifugal separation using a centrifugal force of 700–1,000 G for 10 minutes thereby urging the sealant statically on the interface between serum and clot layers. Thus, as shown in FIG. 9, the sealant, which was thixotropic and had a specific gravity intermediate serum 4 and clot 5, was positioned on the interface between serum 4 and clot 5 to form a gel partition between the two. Since the silica and the nonwoven cloth 7 had specific gravities and were not contained in the serum layer 4. The serum was of a fibrin-free high purity. It was easily removed from the blood-collecting tube by decantation or by suction through a fine nozzle.

As described in detail above, the apparatus for separating blood according to the present invention contains at its bottom a thioxotropic gel-like material for the separation of blood consisting as the principal component an α-olefin-dimaleate copolymer upon the surface of which a cavity has been formed. During the centrifugal separation operation, stress is concentrated at the cavity, and shear force easily and rapidly induces fluidization of the gel-like material. The material can then be transferred toward the separation region by applying a very small centrifugal force. Therefore, when it is used for the separation of blood, blood cells are less liable to injuries and the centrifugal separation takes a shorter operating time. Moreover, the apparatus for separating blood of the invention is advantageous in that it involves transformation of the gel-like sealant only which is simple in production and also, it does not require associated equipment special for raising the gel-like sealant which will increase production cost. In addition, when diameter of the opening of the cavity is from 0.15 to 0.7 times the inner diameter of the tube, and its depth is from 0.13 to 0.65 times the thickness of the gel-like material, the gel-like material can be fluidized satisfactorily using a conventional centrifugal force (1000 G) even if a small amount of blood is collected or a blood-collecting tube with a small diameter is employed. There is no possibility for hemolysis or other adverse reactions to be induced. Also, when the diameter of the openings is from 0.3 to 0.5 times the inner diameter of the tube, and its depth is from 0.2 to 0.55 times the thickness of the gel-like material, fluidity of the gel-like substance can be assured using a centrifugal force of the above-cited magnitude, even if blood from an anemic patient containing a smaller number of blood cells and having a lower specific gravity is used.

Compared with the stress applied to the gel-like material when its upper surface is slanted, the gel-like material with a cavity formed therein is subjected to a greater stress to insure fluidization of the gel-like substance.

When a cavity is formed at a position closer to the wall of the tube, flow of the gel-like material can be directed toward the opposite side of the wall as compared with the cavity positioned at the center, thereby enabling the amount of the gel-like material adhered to the bottom and wall of the tube to be the minimum. Also, hemolysis, which is believed to be due to friction between the gel-like material and blood cells, can be a lesser degree, and blood cells remaining afloat in the upper portion of the gel-like material after centrifugal operation can be in a smaller amount.

Cost of an α-olefin-dimaleate copolymer used as the principal component as described hereinabove is about ⅓ the cost of a silicone fluid. Furthermore, as it is a stable copylymer, there is no possibility for water-repellent substances to be released with a result that water-repellent films are produced within the tube to delay blood coagulation. Since the separation tube is made of glass, its inner surface promotes coagulation upon contact with blood and should be kept clean. Therefore, as compared with the prior-art sealants from which water-repellent films are disadvantageously formed within the separation tube, time required for collecting serum can be reduced. This effect is more remarkable when diatomaceous earth and nonwoven cloth or a clot-promoting agent, as mentioned above, is employed in combination. Reduction in blood coagulation time in the combined use can be as great as about 30 minutes.

Moreover, the gel-like material, which is desirably sterilized if it has been in advance contained in the separation tube, does not undergo any chemical or physical changes which will adversely affect clinical testing when it is subjected to γ-ray sterilization (e.g. dose, 2.5 megarads).

In addition, those α-olefin-dimaleate copolymers which contain a α-olefin component from 4 to 22 carbon atoms and consist of a maleic ester selected from the methyl, ethyl, butyl and 2-ethylhexyl esters (viscosity 10,000–120,000 c.p./25° C.) are stable especially upon aging and can be the main component for the preparation, in combination with auxiliaries such as a viscosity-specific gravity adjusting agent, of such sealants that are readily gelled, easily adjusted to a specific gravity intermediate between serum and the clotted portion and associated with almost no phase segregation and reduced fluidity.

As shown in the above-cited examples of the composition (Example 1), a $C_8$–$C_{24}$ aliphatic amine derivatives of smectite clay or inorganic fine powders such as hydrophobic silica fine powders are used as the viscosity-specific gravity adjusting agent so that a stable thixotropic sealant which is associated with little phase segregation and deterioration in fluidity can be obtained. Among the sealants, those which employ a $C_8$–$C_{24}$ aliphatic amine derivative of smectite clay are conveniently quality controlled because they are not light transmitting and can readily be examined for dispersion with a microscope and the like. As shown in Table 1 for the examples of the composition, use of an aliphatic amine derivative of smectite clay such as quaternary ammonium salts of smectite clay which has a good thickening effect results in stable thixotropic sealants without the use of a gelling agent.

The α-olefin-dimaleate copolymers (A), (B), (C), and (E) among the examples of the composition shown in Tables 1 and 2 above, are n-α-olefin-dimethyl maleate copolymers by the use as the main component of which can easily be produced sealants having a specific gravity closely intermediate serum and the coagulated portion and a desirable viscosity. Therefore, a relatively small amount of the viscosity-specific gravity adjusting agent is required and, moreover, there is little possibility for changes on aging, phase segregation and reduction in fluidity.

In addition, use of the aforementioned wax is especially effective upon prevention of reduction of thixotropy caused by phase segregation in the sealant.

TEST EXAMPLE 1

At the bottom of a 10-ml. cylindrical separation tube 12 mm. in inner diameter was placed ca. 1.7 ml. of a thixotropic gel-like sealant (specific gravity 1.045, viscosity 350,000 c.p. at 25° C.) consisting of silicone oil, silica and an inorganic gelling agent. Into the separation tube was inserted a nozzle tube 3 mm. in inner diameter, from the top of which was jetted air toward the surface of the sealant under a pressure of ca. 4 kg./cm.² There was thus formed a nearly cylindrical cavity (diameter of the opening ca. 7 mm., depth ca. 8 mm.).

Then, 8 ml. of a copper sulfate solution (specific gravity 1.090) was poured into the separation tube, which was subsequently subjected to centrifugal separation at 1100 r.p.m. (ca. 200 G). After 10 minutes, the sealant was completely moved upon the copper sulfate solution to form a layer of a uniform thickness.

For comparison's sake, an operation was conducted under the same conditions as in test Example 1 above except that the centrifugal separation was applied with the upper surface of the sealant maintained flat and without a cavity formed. The gel-like sealant was hardly moved to remain held at the bottom of the tube. It was also found that fluidization of the gel-like sealant in the separation tube to move upward on the copper sulfate required a centrifugal force of at least 500 g.

TEST EXAMPLE 2

The same separation tube and gel-like sealant as in Test Example 1 was used. As shown in FIG. 7, the sealant was placed in the separation tube in such a way that the upper surface was inclined at an angle of about 30° C. from a horizontal position. Then, a cavity of nearly the same size and shape as in Test Example 1 was formed by the use of air jet in the same way as in Test Example 1. The same copper sulfate solution as in Example 1 was poured into the tube, which was then subjected to centrifugal separation at 1100 r.p.m. (ca. 200 G). After 9 minutes, the sealant was completely moved upward on the copper sulfate solution.

For comparison, an operation was conducted under the same conditions as in Test Example 2 above except that the centrifugal separation was applied with the upper surface of the sealant inclined at an angle of ca. 30° from a horizontal position and without a cavity formed. The sealant was moved upward after 9 minutes in an amount about ¾ in Test Example 2.

EXAMPLE 1

At the bottom of a 10-ml. cylindrical separation tube 12 mm. in inner diameter was placed ca. 1.7 ml. of a thixotropic gel-like sealant (specific gravity 1.045, viscosity 350,000 c.p. at 25° C.) consisting of silicone, silica and a gelling agent to a thickness of the gel of 15 mm. Then, a nozzle tube ca. 3 mm. in inner diameter was inserted into the separation tube, and air was jetted through the top of the nozzle tube under a pressure of ca. 4 kg./cm.² toward the upper surface of the sealant. A nearly cylindrical cavity as shown in FIG. 1 (diameter of the opening ca. 7 mm., depth ca. 8 mm.) was formed.

Then, a piece of nonwoven cloth weighing 80 g./m.² (800, Fuji Chemicloth Co., Ltd.) was dipped in an aqueous solution of 8% by weight of a clotting agent (crystalline silica, Min-U-Sil, manufactured by Pensylvania Glass Sand Co.) and 1% by weight of a binder (polyvinylpyrrolidone), dried and punched into a disc 14 mm. in diameter. The disc was placed at a position intermediate the sealant and the open end of the tube and at an angle slightly inclined from a horizontal position. The tube was then sealed at the open end by a rubber closure and evacuated to complete an apparatus for separating blood.

Using the apparatus, blood was collected and coagulated. After completion of the coagulation, the blood was centrifuged at 2000 r.p.m. (ca. 760 G), and the sealant was completely moved upward on the interface between the serum and clot layers. There was obtained clean serum.

EXAMPLE 2

At the bottom of a 7-ml. cylindrical separation tube 10.8 mm. in inner diameter was placed ca. 0.9 ml. of a sealant of the composition 2 in Table 1 above (α-olefin-dimaleate copolymer/Aerosil 200/Bentone 38, specific gravity 1.039, viscosity 620,000 c.p./25° C.). To a thickness of 1.3 mm. at the center. A nearly cylindrical cavity ca. 4 mm. in diameter of the opening and ca. 5 mm. in depth was formed in the same way as in Example 1 above using a nozzle tube ca. 2 mm. in diameter.

A disc of nonwoven cloth with a clot-promoting agent applied (11.6 mm. in diameter) prepared in entirely the same way as in the above example was inserted into the tube to obtain a similar apparatus for separating blood.

Using the apparatus, blood was collected and coagulated. After completion of the coagulation, the blood was centrifuged at 2200 r.p.m. (ca. 920 G). The sealant formed a barrier between the serum and clot layers, and cell and fibrin-free serum was easily isolated.

We claim:
1. Apparatus for separating blood comprising:
a tube with a closed bottom end;
a thixotropic gel-like sealant having a specific gravity intermediate between the gravities of serum and clot phases of blood, said sealant being contained at the bottom end of said tube and having an upper surface spaced from the bottom of said tube; and
a cavity formed in said sealant when said tube is at rest, said cavity being intermediate the edges of said sealant and extending from said upper surface toward the bottom of said tube but not reaching the bottom of said tube, said cavity being formed by said sealant alone without any cavity maintaining members in said tube.

2. The apparatus of claim 1, wherein said thixotropic gel-like sealant contains an adjusting agent for viscosity and specific gravity to provide a specific gravity of said sealant between 1.035 and 1.055.

3. The apparatus of claim 2, wherein said sealant has as its principal component an α-olefin-dimaleate copolymer having a viscosity from 10,000 to 120,000 c.p. at 25° C.

4. The apparatus of claim 3, wherein said cavity has a diameter at the upper surface of said sealant from 0.15 to 0.7 times the inner diameter of the tube, and said cavity has a depth of from 0.13 to 0.65 times the thickness of said sealant in said tube, said thickness being measured from said bottom end of said tube to said upper surface of said sealant.

5. The apparatus of claim 3, wherein said cavity has a diameter at the upper surface of said sealant from 0.15 to 0.7. times the inner diameter of the tube, and said cavity has a depth of from 0.13 to 0.65 times the thickness of said sealant in said tube, said thickness being measured from said bottom end of said tube to said upper surface of said sealant.

6. Apparatus for separating blood according to claim 3 wherein said α-olefin-dimaleate copolymer has the general formula wherein $R_1$ may be the same or different in one molecule and is hydrogen atom or an alkyl group containing from 1 to 20 carbon atoms, $R_2$ and $R_3$ are each straight or branched alkyl group containing from 1 to 15 carbon atoms or a branched alkyl group containing from 16 to 20 carbon atoms, provided that when $R_1$ is hydrogen atom, $R_2$ and $R_3$ are each a straight or branched alkyl group containing from 12 to 15 carbon atoms or a branched alkyl group containing from 16 to 20 carbon atoms, and then $R_1$ is alkyl group having from 1 to 20 carbon atoms, the total numbers of carbon atoms in $R_1$ and $R_2$ groups and $R_1$ and $R_3$ groups are from 5 to 25, respectively, and n is an integer such that the viscosity of said copolymer is from 10,000 to 120,000 c.p. at 25° C.

7. Apparatus for separating blood according to claim 6 wherein $R_1$ in the general formula for said copolymer is an alkyl group containing from 2 to 20 carbon atoms and $R_2$ and $R_3$ are each selected from the group consisting of methyl, ethyl, butyl and 2-ethylhexyl groups.

8. Apparatus for separating blood according to claim 7 wherein $R_1$ is an alkyl group containing from 4 to 20 carbon atoms and $R_2$ and $R_3$ are both methyl group.

9. Apparatus for separating blood according to claim 8 wherein $R_1$ is a combination of alkyl groups containing 10 and 12 carbon atoms.

10. Apparatus for separating blood according to claim 8 wherein $R_1$ is a combination of alkyl groups containing 4 and 6 carbon atoms.

11. Apparatus for separating blood according to claim 8 wherein from 0.04 to 0.6 parts by weight of a gelling agent is contained per 100 parts by weight of an α-olefin-dimaleate copolymer.

12. Apparatus for separating blood according to claim 8 wherein from 1.0 to 3.0 parts by weight of a wax consisting of an α-olefin-dimaleate copolymer containing in the α-olefin component from 30 to 60 carbon atoms is further added to the principal component.

13. Apparatus for separating blood according to claim 2 wherein said adjusting agent for viscosity and specific gravity is at least one member selected from the group consisting of $C_8$–$C_{24}$ aliphatic amine derivatives of smectite clay and inorganic fine powders.

14. Apparatus for separating blood according to claim 13 wherein said adjusting agent is a quaternary ammonium derivative of smectite clay.

15. Apparatus for separating blood according to claim 13 wherein said adjusting agent for viscosity and specific gravity is inorganic fine powders of fumed silica or precipitated silica.

16. The apparatus of claim 2, wherein said cavity has a diameter at the upper surface of said sealant from 0.15 to 0.7 times the inner diameter of the tube, and said cavity has a depth of from 0.13 to 0.65 times the thickness of said sealant in said tube, said thickness being measured from said bottom end of said tube to said upper surface of said sealant.

17. The apparatus of claim 2, wherein said cavity has a diameter at the upper surface of said sealant from 0.15 to 0.7 times the inner diameter of the tube, and said cavity has a depth of from 0.13 to 0.65 times the thickness of said sealant in said tube, said thickness being measured from said bottom end of said tube to said upper surface of said sealant.

18. Apparatus for separating blood according to claim 1 wherein said tube has a closed top end, and further comprising a clot-promoting medium contained at an intermediate position in said tube between said closed top and bottom ends, said clot-promoting medium being comprised of a carrier having a specific gravity higher than blood cells and holding finely divided clot-promoting particles therein.

19. Apparatus for separating blood according to claim 18 wherein said clot-promoting particles are at least one member selected from the group consisting of silica, crystalline silica fine powders, diatomaceous earth, glass fine powders, kaolin and bentonite.

20. Apparatus for separating blood according to claim 18 or 19 wherein said clot-promoting particles are present in an amount from 0.3 to 10.0 mg. per 10 ml. of blood capacity of said apparatus.

21. Apparatus for separating blood according to claim 18 wherein said carrier is cloth, filter paper, non-woven cloth or cotton.

22. Apparatus for separating blood according to claim 18 wherein said clot-promoting medium is located spaced above said upper surface of said sealant.

23. Apparatus for separating blood according to claim 1 wherein said apparatus is evacuated.

24. The apparatus of claim 1, wherein said cavity has a diameter at the upper surface of said sealant from 0.15 to 0.7 times the inner diameter of the tube, and said cavity has a depth of from 0.13 to 0.65 times the thickness of said sealant in said tube, said thickness being measured from said bottom end of said tube to said upper surface of said sealant.

25. The apparatus of claim 1, wherein said cavity has a diameter at said upper surface of from 0.3 to 0.5 times the inner diameter of the tube, and said cavity has a depth of from 0.2 to 0.55 times the thickness of said sealant, said thickness being measured from said bottom end of said tube to said upper surface of said sealant.

* * * * *